US008574659B2

(12) United States Patent
Guo et al.

(10) Patent No.: US 8,574,659 B2
(45) Date of Patent: *Nov. 5, 2013

(54) SUSTAINED RELEASE DRUG DELIVERY DEVICES, METHODS OF USE, AND METHODS OF MANUFACTURING THEREOF

(75) Inventors: Hong Guo, Wayland, MA (US); Paul Ashton, Newton, MA (US)

(73) Assignee: pSivida US, Inc., Watertown, MA (US)

( * ) Notice: Subject to any disclaimer, the term of this patent is extended or adjusted under 35 U.S.C. 154(b) by 43 days.

This patent is subject to a terminal disclaimer.

(21) Appl. No.: 12/688,132

(22) Filed: Jan. 15, 2010

(65) Prior Publication Data

US 2010/0119694 A1    May 13, 2010

Related U.S. Application Data

(63) Continuation of application No. 11/081,142, filed on Mar. 15, 2005, now abandoned, which is a continuation of application No. 10/096,877, filed on Mar. 14, 2002, now abandoned, which is a continuation of application No. 09/558,207, filed on Apr. 26, 2000, now Pat. No. 6,375,972.

(51) Int. Cl.
*A61K 9/50* (2006.01)

(52) U.S. Cl.
CPC .................................... *A61K 9/5089* (2013.01)
USPC .......................................... 427/2.21; 424/426

(58) Field of Classification Search
None
See application file for complete search history.

(56) References Cited

U.S. PATENT DOCUMENTS

| | | |
|---|---|---|
| 3,416,350 A | 12/1968 | Ness |
| 3,618,604 A | 11/1971 | Ness |
| 3,630,200 A | 12/1971 | Higuchi |
| 3,632,739 A | 1/1972 | Kornblum |
| 3,829,570 A | 8/1974 | Heider et al. |
| 3,854,480 A | 12/1974 | Zaffaroni |
| 3,896,819 A | 7/1975 | Zaffaroni et al. |
| 3,916,899 A | 11/1975 | Theeuwes et al. |
| 3,948,254 A | 4/1976 | Zaffaroni |

(Continued)

FOREIGN PATENT DOCUMENTS

| | | |
|---|---|---|
| CA | 2544460 A1 | 5/2001 |
| CN | 1200033 A | 11/1998 |

(Continued)

OTHER PUBLICATIONS

Baker et al., In Vitro and In Vivo Evaluation of Intravitreal Sustained Release Dexamethasone Devices; IOVS 34(4): 121-122 (1993).

(Continued)

*Primary Examiner* — Bethany Barham
(74) *Attorney, Agent, or Firm* — Ropes & Gray LLP; David P. Halstead; David P. Pleynet

(57) ABSTRACT

A method and device for treating a mammalian organism to obtain a desired local or systemic physiological or pharmacological effect is provided. The method includes administering a sustained release drug delivery system to a mammalian organism in need of such treatment at an area wherein release of an effective agent is desired and allowing the effective agent to pass through the device in a controlled manner. The device includes an inner core or reservoir including the effective agent, an impermeable tube which encloses portions of the reservoir, and a permeable member at an end of the tube.

6 Claims, 3 Drawing Sheets

(56) References Cited

U.S. PATENT DOCUMENTS

| | | |
|---|---|---|
| 3,961,628 A | 6/1976 | Arnold |
| 3,977,404 A | 8/1976 | Theeuwes |
| 3,980,463 A | 9/1976 | Muramoto et al. |
| 3,993,071 A | 11/1976 | Higuchi et al. |
| 4,008,719 A | 2/1977 | Theeuwes et al. |
| 4,014,334 A | 3/1977 | Theeuwes et al. |
| 4,014,335 A | 3/1977 | Arnold |
| 4,014,355 A | 3/1977 | DiMatteo et al. |
| 4,034,758 A | 7/1977 | Theeuwes |
| 4,036,227 A | 7/1977 | Zaffaroni et al. |
| 4,077,407 A | 3/1978 | Theeuwes et al. |
| 4,111,201 A | 9/1978 | Theeuwes |
| 4,111,203 A | 9/1978 | Theeuwes |
| 4,135,514 A | 1/1979 | Zaffaroni et al. |
| 4,142,526 A | 3/1979 | Zaffaroni et al. |
| 4,177,256 A | 12/1979 | Michaels et al. |
| 4,186,184 A | 1/1980 | Zaffaroni |
| 4,200,098 A | 4/1980 | Ayer et al. |
| 4,247,498 A | 1/1981 | Castro |
| 4,256,108 A | 3/1981 | Theeuwes |
| 4,260,736 A | 4/1981 | Asano et al. |
| 4,283,394 A | 8/1981 | West et al. |
| 4,290,426 A | 9/1981 | Luschen et al. |
| 4,304,232 A | 12/1981 | Michaels |
| 4,304,765 A | 12/1981 | Shell et al. |
| 4,322,323 A | 3/1982 | Capozza |
| 4,326,525 A | 4/1982 | Swanson et al. |
| 4,327,725 A | 5/1982 | Cortese et al. |
| 4,351,337 A | 9/1982 | Sidman |
| 4,439,196 A | 3/1984 | Higuchi |
| 4,475,916 A | 10/1984 | Himmelstein |
| 4,478,818 A | 10/1984 | Shell et al. |
| 4,484,922 A | 11/1984 | Rosenwald |
| 4,519,801 A | 5/1985 | Edgren |
| 4,519,909 A | 5/1985 | Castro |
| 4,522,625 A | 6/1985 | Edgren |
| 4,609,374 A | 9/1986 | Ayer |
| 4,615,698 A | 10/1986 | Guittard et al. |
| 4,624,847 A | 11/1986 | Ayer et al. |
| 4,627,850 A | 12/1986 | Deters et al. |
| 4,652,441 A | 3/1987 | Okada et al. |
| 4,657,543 A | 4/1987 | Langer et al. |
| 4,673,405 A | 6/1987 | Guittard et al. |
| 4,681,755 A | 7/1987 | Columbo et al. |
| 4,692,336 A | 9/1987 | Eckenhoff et al. |
| 4,693,886 A | 9/1987 | Ayer |
| 4,711,782 A | 12/1987 | Okada et al. |
| 4,716,031 A | 12/1987 | Eckenhoff et al. |
| 4,717,567 A | 1/1988 | Wu et al. |
| 4,720,384 A | 1/1988 | DiLuccio et al. |
| 4,730,013 A | 3/1988 | Bondi et al. |
| 4,740,365 A | 4/1988 | Yukimatsu et al. |
| 4,743,247 A | 5/1988 | Wong |
| 4,764,364 A | 8/1988 | Heller et al. |
| 4,777,049 A | 10/1988 | Magruder et al. |
| 4,786,500 A | 11/1988 | Wong |
| 4,789,513 A | 12/1988 | Cloeren |
| 4,806,382 A | 2/1989 | Goldberg et al. |
| 4,814,323 A | 3/1989 | Andrieu et al. |
| 4,830,860 A | 5/1989 | Ranade |
| 4,832,957 A | 5/1989 | Dempski et al. |
| 4,839,177 A | 6/1989 | Columbo et al. |
| 4,839,342 A | 6/1989 | Kaswan |
| 4,861,627 A | 8/1989 | Mathiowitz et al. |
| 4,863,455 A | 9/1989 | Whitehead |
| 4,863,735 A | 9/1989 | Kohn et al. |
| 4,865,846 A | 9/1989 | Kaufman |
| 4,877,618 A | 10/1989 | Reed, Jr. |
| 4,882,150 A | 11/1989 | Kaufman |
| 4,889,720 A | 12/1989 | Konishi |
| 4,891,223 A | 1/1990 | Ambegaonkar et al. |
| 4,898,733 A | 2/1990 | DePrince et al. |
| 4,913,906 A | 4/1990 | Friedman et al. |
| 4,927,632 A | 5/1990 | Wong |
| 4,927,687 A | 5/1990 | Nuwayser |
| 4,945,089 A | 7/1990 | Clark |
| 4,946,456 A | 8/1990 | Roth et al. |
| 4,952,402 A | 8/1990 | Sparks et al. |
| 4,959,217 A | 9/1990 | Sanders et al. |
| 4,994,273 A | 2/1991 | Zentner et al. |
| 5,028,435 A | 7/1991 | Katz et al. |
| 5,035,891 A | 7/1991 | Runkel et al. |
| 5,088,505 A | 2/1992 | De Nijs et al. |
| 5,091,185 A | 2/1992 | Castillo et al. |
| 5,098,443 A | 3/1992 | Parel et al. |
| 5,102,389 A | 4/1992 | Hauser |
| 5,120,548 A | 6/1992 | McClelland et al. |
| 5,124,392 A | 6/1992 | Robertson et al. |
| 5,141,752 A | 8/1992 | Ayer et al. |
| 5,147,647 A | 9/1992 | Darougar |
| 5,156,623 A | 10/1992 | Hakamatsuka et al. |
| 5,174,999 A | 12/1992 | Magruder et al. |
| 5,201,764 A | 4/1993 | Kelman et al. |
| 5,213,808 A | 5/1993 | Bar-Shalom et al. |
| 5,226,902 A | 7/1993 | Bae et al. |
| 5,294,604 A | 3/1994 | Nussenblatt et al. |
| 5,314,419 A | 5/1994 | Pelling |
| 5,342,622 A | 8/1994 | Williams et al. |
| 5,378,475 A | 1/1995 | Smith et al. |
| 5,389,382 A | 2/1995 | List et al. |
| 5,393,536 A | 2/1995 | Brandt et al. |
| 5,411,952 A | 5/1995 | Kaswan |
| 5,413,572 A | 5/1995 | Wong et al. |
| 5,431,921 A | 7/1995 | Thombre |
| 5,435,998 A | 7/1995 | Abelson |
| 5,443,505 A | 8/1995 | Wong et al. |
| 5,474,979 A | 12/1995 | Ding et al. |
| 5,476,511 A | 12/1995 | Gwon et al. |
| 5,482,934 A | 1/1996 | Calatayud et al. |
| 5,512,293 A | 4/1996 | Landrau et al. |
| 5,543,441 A | 8/1996 | Rhee et al. |
| 5,554,187 A | 9/1996 | Rizzo, III |
| 5,569,429 A | 10/1996 | Luker |
| 5,573,775 A | 11/1996 | Robertson et al. |
| 5,593,697 A | 1/1997 | Barr et al. |
| 5,618,560 A | 4/1997 | Bar-Shalom et al. |
| 5,639,275 A | 6/1997 | Baetge et al. |
| 5,650,170 A | 7/1997 | Wright et al. |
| 5,665,373 A | 9/1997 | Robertson et al. |
| 5,753,234 A | 5/1998 | Lee et al. |
| 5,766,242 A | 6/1998 | Wong et al. |
| 5,770,589 A | 6/1998 | Billson et al. |
| 5,773,019 A | 6/1998 | Ashton et al. |
| 5,830,546 A | 11/1998 | Ehret et al. |
| 5,840,335 A | 11/1998 | Wenzel et al. |
| 5,840,881 A * | 11/1998 | Uda et al. .................. 536/46 |
| 5,851,547 A | 12/1998 | Fujioka et al. |
| 5,902,598 A | 5/1999 | Chen et al. |
| 5,989,581 A | 11/1999 | Groenewegen |
| 5,998,431 A | 12/1999 | Tseng et al. |
| 6,039,975 A | 3/2000 | Shah et al. |
| 6,051,576 A | 4/2000 | Ashton et al. |
| 6,120,791 A | 9/2000 | Aguadisch et al. |
| 6,120,802 A | 9/2000 | Breitenbach et al. |
| 6,123,861 A | 9/2000 | Santini, Jr. et al. |
| 6,217,895 B1 | 4/2001 | Guo et al. |
| 6,242,058 B1 | 6/2001 | Bahadur et al. |
| 6,267,154 B1 | 7/2001 | Felicelli et al. |
| 6,283,951 B1 | 9/2001 | Flaherty et al. |
| 6,331,313 B1 | 12/2001 | Wong et al. |
| 6,368,658 B1 | 4/2002 | Schwarz et al. |
| 6,375,972 B1 | 4/2002 | Guo et al. |
| 6,441,047 B2 | 8/2002 | DeSantis, Jr. |
| 6,491,683 B1 | 12/2002 | Dong et al. |
| 6,548,078 B2 | 4/2003 | Guo et al. |
| 6,719,751 B2 | 4/2004 | Dong et al. |
| 6,916,788 B2 | 7/2005 | Seo et al. |
| 7,563,255 B2 | 7/2009 | Adamis et al. |
| 2002/0119197 A1 | 8/2002 | Dyar et al. |
| 2003/0105121 A1 | 6/2003 | Bihari |

(56) References Cited

U.S. PATENT DOCUMENTS

| | | |
|---|---|---|
| 2004/0009222 A1 | 1/2004 | Chou et al. |
| 2004/0176341 A1 | 9/2004 | Chou et al. |
| 2010/0080830 A1 | 4/2010 | Ashton et al. |

FOREIGN PATENT DOCUMENTS

| | | |
|---|---|---|
| EP | 0 147 780 A2 | 7/1985 |
| EP | 0 180 708 A1 | 5/1986 |
| EP | 0 316 838 A1 | 5/1989 |
| EP | 0 462 959 A1 | 12/1991 |
| EP | 0861659 A1 | 9/1998 |
| EP | 0891769 A1 | 1/1999 |
| HU | 210 461 | 4/1995 |
| JP | 58035110 A | 3/1983 |
| JP | 07-048246 A | 2/1995 |
| JP | 8253426 A | 10/1996 |
| JP | 10-182499 A | 7/1998 |
| TW | 396043 | 7/2000 |
| TW | 470655 | 1/2002 |
| WO | WO-84/00296 A1 | 2/1984 |
| WO | WO-91/11176 A1 | 8/1991 |
| WO | WO-92/07556 A1 | 5/1992 |
| WO | WO-9418956 A1 | 9/1994 |
| WO | WO-95/20567 A1 | 8/1995 |
| WO | WO-9535131 A1 | 12/1995 |
| WO | WO-97/11655 A1 | 4/1997 |
| WO | WO-97/15293 A2 | 5/1997 |
| WO | WO-98/42317 A2 | 10/1998 |
| WO | WO-98/43611 A1 | 10/1998 |
| WO | WO-99/11244 A1 | 3/1999 |
| WO | WO-01/80825 A2 | 11/2001 |
| WO | WO-02/05788 | 1/2002 |
| WO | WO-02/087586 A1 | 11/2002 |
| WO | WO-03/094888 A1 | 11/2003 |

OTHER PUBLICATIONS

Barre-Sinoussi, et al., Science, 220:868-70 (1983).
Beer et al., Intraocular concentration and pharmacokinetics of triamcinolone acetonide after a single intravitreal injection; Ophthalmology 110(4): 681-6 (2003).
Blanford et al., 5-Fluorouracil Sustained Release Device Implantation: Toxicology and Histology in Rabbits, Invest. Opthal. and vis. Sci. 31(4):591, abstr. 2893-89 (1990). (Abstract).
Challa, et al. Exudative Macular Degeneration and Intravitreal Triamcinolone: 18 Month Follow Up. Australian and New Zealand Journal of Ophthalmology, 26(4):277-281 (1998).
Cheng et al., Intravitreal Sustained-Release Dexamethasone Device in the Treatment of Experimental Uveitis; Invest. Ophthal. & Visual Science 36(2): 442-453 (1995).
Dalgleish, et al., Nature, 312:763-67 (1984).
Database WPI, Week 7943, Derwent Publications Ltd., London, GB; AN 79-78139b XP002065720 & JP 54119 020 (Nippon Kayaku KK), Sep. 14, 1979 (Absract).
Driot et al.,Ocular Pharmacokinetics of fluocinolone acetonide after Retisert intravitreal implantation in rabbits over a 1-year period; J Ocul Pharm. Ther 20(3): 269-75 (2004).
European Search Report for EP 08 16 1489 mailed Jun. 15, 2009.
Gallo, et al., Science, 224:500-3 (1984).
Goins et al., "Intravitreal Sustained Release of Gancyclovir," Invest. Opthal. and Vis. Sci. 31(4):364, abstr. 1791 (1990). (Abstract).
Hainsworth et al., Sustained Release Intravitreal Dexamethasone; J. Ocular Pham and Ther. 12: 57-63 (1996).
Jaffe et al. Safety, Efficacy, and Pharmacokinetics of an Intravitreal, Fluocinolone Sustained Drug Delivery System. Investigative Ophthalmology & Visual Science. 40(4):S988. (1999).
Jaffe et al., Dexamethasone Sustained Drug Delivery Implant for the Treatment of Sever Uveitis; Brief Reports 20(4): 402-403 (2000).
Klatzmann, et al., Nature, 312:767-68 (1984).
Maddon, et al., Cell, 47:333-48 (1986).
Newell et al., Clearance and Metabolism of Intravitreal Triamcinolone; IOVS 34(4): 116 (1993).
Pearson et al. Clearance and Distribution of Ciprofloxacin After Intravitreal Injection. Retina. 13(4):326-330. (1993).
Pearson et al. Evaluation of a Delivery System Providing Long-Term Release of Cyclosporine. Arch Ophthamology. 114:311-17 (1996).
Pearson et al., "Polyvinyl Alcohol Membrane Permeability Characteristics of Gancyclovir," Invest. Opthal. and Vis. Sci. 30(4):511, abstr. 42 (1989). (Abstract).
Pearson et al., Proceed. Intern. Symp. Control Rel. Bioch. Mater. 17 (1990) Controlled Release Society, Jul. 22-25, pp. 470, 171.
Perasalo. The Prevalence of Macular Degeneration in a Cohort of Institutionalized Geriatric Glaucoma Patients. Acta Ophthamology. 72(2):175-77 (1994).
Rafii et al., Pharmacokinetics of Sustained-Release Implantable Devices of Acetazolamide; IOVA 34(4): 121-122 (1993).
Smith et al., "A Membrane Based Sustained Release Ocular Delivery System for 5-Fluorouracil," Invest. Opthal. and Vis. Sci. 30(4):271, abstr. 37 (1989) (Abstract).
Smith et al., "Intraocular Sustained Release of Antiviral Agents in AIDS," Proceed. Intern. Symp. Contol. Rel. Bioact. Mater. 17:470-471 (1990).
Smith et al., "Polyvinyl Alcohol Membrane Permeability Characteristics of 5-Fluorouracil," Journal of Ocular Pharmacology 4(2):147-152 (1988).
Solomon et al., "Sustained Release Drug Delivery Systems in Extracapsular Cataract Surgery," Invest. Opthal. and Vis. Sci. 31(4):351 Abstr. 1724-19 (1990) (Abstract).
U.S. Appl. No. 10/714,549, filed Nov. 13, 2003, Chou et al.
U.S. Appl. No. 60/482,677, filed Jun. 26, 2003, Su et al.
U.S. Appl. No. 60/501,947, filed Sep. 11, 2003, Guo et al.
Wu, X. S., Control Drug Delivery Systems (Part I), 1966, Technomic Publishing Co., Inc., pp. 32, 33, 44-46, 63, 66, and 67.
International Search Report for PCT/US2004/035430 dated Aug. 12, 2005.
International Search Report for PCT/US01/12700 mailed Apr. 18, 2002.
International Search Report for PCT/US00/07513 mailed Aug. 30, 2000.
M. Kajhara, et al., "Development of a new drug delivery system for protein drugs using silicone (II)," Journal of Controlled Release, 73:279-291 (2001).
Yang et al., An Intravitreal Sustained-Release Triamcinolone and 5-Fluorouracil Codrug in the Treatment of Experimental Proliferative Vitreoretinopathy, Arch Opthalmol, 116:69-77 (1998).
Goodman & Gilman's The Pharmacological Basis of Therapeutics, 1996, "Adrenocorticotropic Hormone; Adrenocortical Steroids and their synthetic analogs; inhibitors of the synthesis and actions of synthesis and actions of adrenocortical hormones", Schimmer, B.P. and Parker, K.L., chapter 59, pp. 1459, 1473, 1474, 1480, and "Ocular Pharmacology", Moroi, S.E. and Lichter, P.R. chapter 65, pp. 1619, 1636 and 1637.
Haynes et al., "Effect of Inhibitors of Arachidonic Acid Metabolism on Corneal Neovascularization in the Rat," Investigative Ophthalmology & Visual Science, 30(7):1588-1593 (1989).
Tano et al., "Inhibition of Intraocular Proliferations With Intravitreal Corticosteriods," American Journal of Ophthalmology, 89(1):131-135 (1980).

\* cited by examiner

SUSTAINED RELEASE DRUG DELIVERY DEVICES, METHODS OF USE, AND METHODS OF MANUFACTURING THEREOF

CROSS REFERENCE TO RELATED APPLICATIONS

This application is a continuation of U.S. application Ser. No. 11/081,142, filed Mar. 15, 2005, which is a continuation of U.S. application Ser. No. 10/096,877, filed Mar. 14, 2002, which is a continuation of U.S. application Ser. No. 09/558,207, filed Apr. 26, 2000, now U.S. Pat. No. 6,375,972. The entire teachings of the above referenced applications are incorporated herein by reference and without disclaimer.

This application is related to U.S. Patent application Ser. No. 08/919,221, by Chen et al., filed Aug. 28, 1997, entitled Sustained Release Drug Delivery Devices, now U.S. Pat. No. 5,902,598, which is incorporated herein by reference in its entirety.

BACKGROUND OF THE INVENTION

1. Field of the Invention

The present invention relates to a novel sustained release drug delivery device, and more particularly to a multilayered drug delivery device.

2. Brief Description of the Related Art

Over the years, various drugs have been developed to assist in the treatment of a wide variety of ailments and diseases. However, in many instances such drugs are not capable of being administered either orally or intravenously without the risk of various deleterious side effects.

For example, intravenous ganciclovir (GCV) is effective in the treatment of cytomegalovirus (CMV) retinitis in AMS patients, but bone marrow toxicity limits its usefulness. The incidence of neutropenia (absolute neutrophil count <1000) during intravenous GCV therapy ranges from 30 to 50%. Continuous maintenance GCV therapy is necessary to prevent progression or recrudescence of the disease, but despite maintenance therapy, 30 to 50% of patients experience a relapse during treatment. Other problems associated with systemic GCV administration include the risk of sepsis related to permanent indwelling catheters and the inability to receive concurrent therapy with zidovudine (AZT) which has been shown to prolong life and improve the immune function in AIDS patients.

Intravitreal GCV injections of 200 to 400 µg administered once or twice weekly have resulted in temporary remission of CMV retinitis in AIDS patients. Intravitreal GCV injections may provide a higher intraocular drug concentration than systemic therapy and reduce the incidence of neutropenia. Current treatment of CMV retinitis in AIDS patients is clearly suboptimal. Ganciclovir is virustatic and thus disease inhibition requires maintenance drug administration.

Due to the risks that certain drugs impose, researchers have developed systems for administering such drugs to aid in the treatment of these ailments and diseases. Many of these systems provide a release rate which reduces the occurrence of detrimental side effects.

With conventional dosing (tablets, injections, etc.), the concentration of drug in a given area of the body increases through an ineffective concentration to some concentration that is effective. Frequently the concentration may actually reach some toxic threshold. After a relatively short period, however, the drug concentration decreases as drug is either metabolized in the body or is eliminated. Frequently, drug levels-decrease so low that therapeutic levels are no longer maintained. A second dose is then given and the cycle is repeated. The goal of sustained release systems is to maintain drug levels within the therapeutic range and ideally a constant level.

In order to achieve constant levels, drugs should be released from a delivery system at a rate that does not change with time (so called zero-order release). In many systems, however, the release rate is proportional to time (i.e., "first order") or the square root of time (or Fickian).

Linear release is achievable with some types of reservoir systems, such as tubes, fibers laminates, or microspheres. In these systems, a drug reservoir is coated in a rate controlling membrane. Drug diffusion across the membrane is rate limiting and is constant (zero order) as long as the membrane's permeability does not change and as long as the concentration of drug in the reservoir is constant (i.e. as long as there is an excess of drug in the reservoir).

In matrix systems, drug is dispersed throughout a matrix and is released as it dissolves and diffuses through the matrix. A drug is released from the outer surface of the matrix first, this layer becomes depleted, and drug that is released from further within the core of the device must then diffuse through the depleted matrix. The net result is that the release rate slows down and Fickian release is common. With matrix systems, zero-order release is very difficult to achieve. The same principles apply to release from gels.

In some bioerodible systems, diffusion through the matrix is designed to be extremely slow and drugs are intended to be released as the system is degraded. It has been generally found to be extremely difficult to use this approach to achieve a zero-order release, as most polymers do not undergo zero-order degradation. "S" type kinetics are more common. A general discussion of drug delivery control systems is provided in Controlled Drug Delivery Systems (Part I), Xue Shen Wu, Ph.D. pp. 32, 33, 44-46, 63, 66, and 67 (Technomic Publishing Co, Inc., 1996), the entire contents of which are incorporated herein by reference.

One such delivery device is an orally administered pill or capsule which contains a drug encapsulated within various layers of a composition that dissolves over a period of time in the digestive tract, thereby allowing a gradual or slow release of the drug into the system.

Another type of device for controlling the administration of such drugs is produced by coating a drug with a polymeric material permeable to the passage of the drug to obtain the desired effect. Such devices are particularly suitable for treating a patient at a specific local area without having to expose the patient's entire body to the drug. This is advantageous because any possible side effects of the drug could be minimized.

Such systems are particularly suitable for treating ailments affecting the eye. Advances for administering a drug to the external surface of the eye are disclosed in U.S. Pat. No. 4,014,335, to Arnold. Arnold describes various ocular inserts that act as a deposit or drug reservoir for slowly releasing a drug into the tear film for prolonged periods of time. These inserts are fabricated of a flexible polymeric material that is biologically inert, non-allergenic, and insoluble in tear fluid. To initiate the therapeutic programs of these devices, the ocular inserts are placed in the cul-de-sac between the sclera of the eyeball and the eyelid for administering the drug to the eye.

Devices formed of polymeric materials that are insoluble in tear fluid retain their shape and integrity during the course of the needed therapy to serve as a drug reservoir for continuously administering a drug to the eye and the surrounding tissues at a rate that is not effected by dissolution or erosion of the polymeric material. Upon termination of the desired therapeutic program, the device is removed from the cul-de-sac.

Another type of device used for sustained release of a drug to the external surface of the eye, described in U.S. Pat. No. 3,416,530, is manufactured with a plurality of capillary openings that communicate between the exterior of the device and the interior chamber, which generally defined from a polymeric membrane. While these capillary openings in this construction are effective for releasing certain drugs to the eye, they add considerable complexity to the manufacture of the device because it is difficult to control the size of these openings in large scale manufacturing using various polymers.

Another device, described in U.S. Pat. No. 3,618,604, does not involve such capillary openings, but instead provides for the release of the drug by diffusion through a polymeric membrane. The device, in a preferred embodiment, as disclosed in that patent, comprises a sealed container having the drug in an interior chamber. Nonetheless, as described in U.S. Pat. No. 4,014,335, certain problems have been identified with such devices such as the difficult task of sealing the margins of the membrane to form the container. In addition, stresses and strains introduced into the membrane walls from deformation during manufacturing of those devices may cause the reservoir to rupture and leak.

Another such device, described in U.S. Pat. No. 4,014,335, comprises a three-layered laminate having a pair of separate and discrete first and third walls formed of a material insoluble in tear fluid with one of the walls formed of a drug release material permeable to the passage of drug and the other wall formed of a material impermeable to the passage of the drug.

The above described systems and devices are intended to provide sustained release of drugs effective in treating patients at a desired local or systemic level for obtaining certain physiological or pharmacological effects. However, there are many disadvantages associated with their use including the fact that it is often times difficult to obtain the desired release rate of the drug. The need for a better release system is especially significant in the treatment of CMV retinitis.

Prior to the development of the present invention, there was developed a novel sustained release delivery device which ameliorated many of the aforementioned problems associated with drug delivery. The device, which is disclosed in U.S. Pat. No. 5,378,475 (incorporated herein by reference in its entirety), included a first coating essentially impermeable to the passage of the effective agent and a second coating permeable to the passage of the effective agent. In the device, the first coating covered at least a portion of the inner core; however, at least a small portion of the inner core is not coated with the first coating layer. The second coating layer essentially completely covers the first coating layer and the uncoated portion of the inner core. The portion of the inner core which is not coated with the second coating layer allows passage of the agent into the second coating layer thus allowing controlled release.

While the devices described in U.S. Pat. No. 5,378,475 solve many of the aforementioned problems pertaining to drag delivery, the devices and the method of making the devices are not without problems. In particular, polymers suitable for coating the inner core are frequently relatively soft and technical difficulties can arise in production of uniform films. This is especially true when attempting to coat non-spherical bodies with edges (such as a cylindrical shape). In such case, relatively thick films must be applied to achieve uninterrupted and uniform coatings, which adds significant bulk to the device. Thus, the devices tend to be larger than necessary as a result of the thickness needed to seal the ends of the inner core.

The aforementioned U.S. Pat. No. 5,902,598 presents solutions to the problems of manufacturing devices which are sized to be effective drug administration devices in anatomical locations where device volume plays a limiting role in the design of the device. While effective in delivering drugs in situ, some manufacturing difficulties have limited scaled up manufacturing of these devices. For example, the impermeable inner coating layer of the devices of the aforementioned application, which immediately surrounds the drug reservoir, is typically formed of a material the thickness of which results in a layer which is not capable of supporting its own weight.

While beneficial from the standpoint of reducing the overall size of the device, and while still sealing the drug reservoir, goals well-addressed in the aforementioned patent, the relative flaccidity of this inner layer makes it difficult to load the device's reservoir with a drug solution, drug slurry, or drug suspension. Because this inner layer is essentially structurally incapable of maintaining its shape without significant collapse, i.e., does not have the dimensional stability or structural ability to accept a drug core inserted therein without changing shape, a relatively solid drug or drug-containing mixture must be used in order to manufacture the device. Loading a drug slurry onto this inner layer during manufacture which does not hold its own shape results in the combination of the drug slurry and inner layer being extremely difficult to handle without damaging it, because the inner layer collapses and the drug-containing mixture flows out.

The problem of device size is extremely important in the design of devices for implantation into limited anatomical spaces such as the eye. Larger devices require more complex surgery to both implant and remove. The increased complexity may result in complications, longer healing or recovery periods, and potential side effects (e.g., increased chance of astigmatism). Furthermore, the extra polymer required to achieve a uniform coating reduces the potential volume of the implant and hence limits the amount of drug that can be delivered, potentially limiting both efficacy and duration.

As a result of all of the above, there remains a need in the art for improving the design and the method of preparing devices which provide a sustained release of a drug to a patient to obtain a desired local or systemic physiological or pharmacological effect especially for ocular use.

SUMMARY OF THE INVENTION

It is, therefore, a primary objective of the present invention to provide a device suitable for the controlled and sustained release of a composition effective in obtaining a desired local or systemic physiological or pharmacological effect.

Another object of the present invention is to provide a method for treating a mammalian organism, e.g., human, to obtain a desired local or systemic physiological or pharmacological effect. The method includes positioning the sustained released drug delivery system at an area wherein release of the agent is desired and allowing the agent to pass through the device to the desired area of treatment.

Another object of the present invention is to provide an ocular device suitable for direct implantation into the vitreous of the eye. Such devices of the present invention are surprisingly found to provide sustained controlled release of various compositions to treat the eye without risk of detrimental local and systemic side effects.

Another object of the present invention is to maximize the amount of drug contained in an intraocular device while minimizing its size in order to prolong the duration of the implant.

Another object of the present invention is to provide an ocular delivery system that could be applied to an intra-ocular lens to prevent inflammation or posterior capsular opacification.

Another object of the present invention is to provide an ocular delivery system that could be inserted directly into the vitreous, under the retina, or onto the sclera, and wherein inserting can be achieved by injecting the system or surgically implanting the system.

According to a first exemplary embodiment, a sustained release drug delivery system comprises an inner reservoir comprising an effective amount of an agent effective in obtaining a desired local or systemic physiological or pharmacological effect, an inner tube impermeable to the passage of said agent, said inner tube having first and second ends and covering at least a portion of said inner reservoir, said inner tube sized and formed of a material so that said inner tube is capable of supporting its own weight, an impermeable member positioned at said inner tube first end, said impermeable member preventing passage of said agent out of said reservoir through said inner tube first end, and a permeable member positioned at said inner tube second end, said permeable member allowing diffusion of said agent out of said reservoir through said inner tube second end.

According to a second exemplary embodiment, a method for treating a mammalian organism to obtain a desired local or systemic physiological or pharmacological effect comprises administering a sustained release drug delivery system to a mammalian organism in need of such treatment.

According to a third exemplary embodiment, a method for treating a mammalian organism for ocular edema and ocular neovascularization comprises administering a sustained release drug delivery system to a mammalian organism in need of such treatment, the drug delivery system reservoir comprising an effective amount of a steroid effective to obtain a desired local or systemic physiological or pharmacological effect.

According to a fourth exemplary embodiment, a method for providing controlled and sustained administration of an agent effective in obtaining a desired local or systemic physiological or pharmacological effect comprises surgically implanting a sustained release drug delivery system at a desired location.

According to a fifth exemplary embodiment, a method of manufacturing a sustained drug delivery system comprises the steps of joining an end member to a length of tube to form a vessel-shaped member the end member selected from the group consisting of an impermeable cap and a permeable plug, positioning a reservoir in the vessel-shaped member, the reservoir containing an effective amount of an effective agent, and forming an outer layer around a portion of the vessel-shaped member, the outer layer formed of a material selected from the group consisting of a permeable material and an impermeable material.

Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to preferred embodiments of the apparatus and method, given only by way of example, and with reference to the accompanying drawings, in which.

DETAILED DESCRIPTION OF THE PREFERRED EMBODIMENTS OF THE INVENTION

Figure 1:
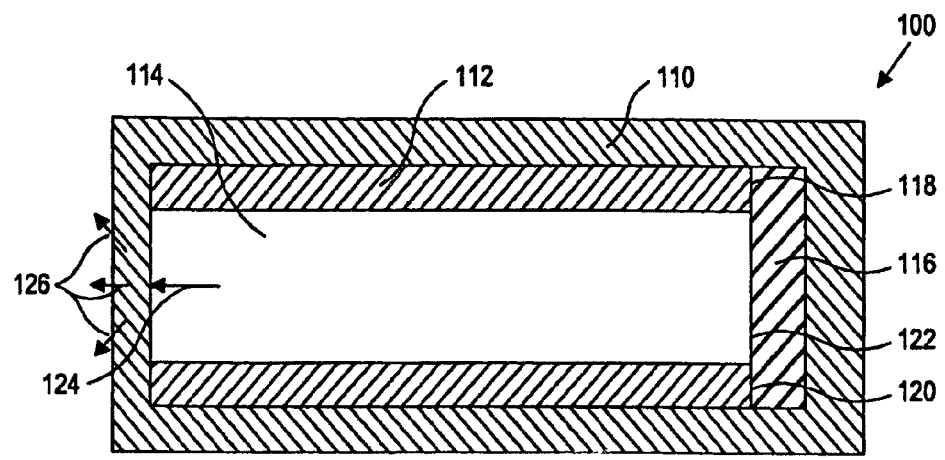
FIG. 1 is an enlarged cross-sectional illustration of one embodiment of a sustained release drug delivery device in accordance with the present invention.

Referring to the drawing figures, like reference numerals designate identical or corresponding elements throughout the several figures.

More specifically, the present inventors have discovered a device and method of preparation thereof that is suitable for the controlled and sustained release of an agent or drug effective in obtaining a desired local or systemic physiological or pharmacological effect. In particular, it has been found that by sealing at least one surface of a reservoir of the device with an impermeable member which is capable of supporting it's own weight, which has dimensional stability, which has the ability to accept a drug core therein without changing shape, and/or retains its own structural integrity so that the surface area for diffusion does not significantly change, manufacture of the entire device is made simpler and the device is better able to deliver a drug.

That is, the use of a tube of material to hold the drug reservoir during manufacture allows for significantly easier handling of the tube and reservoir, because the tube fully supports both its own weight and the weight of the reservoir. Thus, the tube used in the present invention is not a coating, because a coating cannot support its own weight. Also, this rigid structure allows the use of drug slurries drawn into the tube, which allows the fabrication of longer cylindrical devices. Furthermore, because of the relative ease of manufacturing devices in accordance with the present invention, more than one reservoir, optionally containing more than one drug, can be incorporated into a single device.

During use of the devices, because the size, shape, or both, of the drug reservoir typically changes as drug diffuses out of the device, the tube which holds the drug reservoir is sufficiently strong or rigid to maintain a diffusion area so that the diffusion rate from the device does not change substantially because of the change in the drug reservoir. By way example and not of limitation, an exemplary method of ascertaining if the tube is sufficiently rigid is to form a device in accordance with the present invention, and to measure the diffusion rate of the drug from the device over time. If the diffusion rate changes more than 50% from the diffusion rate expected based on the chemical potential gradient across the device at any particular time, the tube has changed shape and is not sufficiently rigid. Another exemplary test is to visually inspect the device as the drug diffuses over time, looking for signs that the tube has collapsed in part or in full.

The use of permeable and impermeable tubes in accordance with the present invention provides flow resistance to reverse flow, i.e., flow back into the device. The tube or tubes assist in preventing large proteins from solubilizing the drug in the drug reservoir. Also, the tube or tubes assist in preventing oxidation and protein lysis, as well as preventing other biological agents from entering the reservoir and eroding the drug therein.

Turning now to the drawing figures, FIG. 1 illustrates a longitudinal cross sectional view of a drug delivery device 100 in accordance with the present invention. Device 100 includes an outer layer 110, an inner tube 112, a reservoir, drug core, drug supply, drug depot, drug matrix, and/or drug in suspension 114, and an inner cap 116. Outer layer 110 is preferably a permeable layer, that is, the outer layer is permeable to the drug contained within reservoir 114. Cap 116 is positioned at one end of tube 112. Cap 116 is preferably formed of an impermeable material, that is, the cap is not permeable to the drug contained within reservoir 114. Cap 116 is joined at end 118, 120 of inner tube 112, so that the cap and the inner tube together close off a space in the tube in which reservoir 114 is positioned, and together the cap and inner tube form a cup- or vessel-shaped member. Inner tube 112 and cap 116 can be formed separately and assembled together, or the inner tube and the cap can be formed as a single, integral, monolithic element.

Outer layer 110 at least partially, and preferably completely, surrounds both tube 112 and cap 116, as illustrated in FIG. 1. While it is sufficient for outer layer 110 to only partially cover tube 112 and cap 116, and in particular the opposite ends of device 100, the outer layer is preferably formed to completely envelop both the tube and cap to provide structural integrity to the device, and to facilitate further manufacturing and handling because the device is less prone to break and fall apart. While FIG. 1 illustrates cap 116 having an outer diameter the same as the outer diameter of inner tube 112, the cap can be sized somewhat smaller or larger than the outer diameter of the inner tube within the spirit and scope of the present invention.

Reservoir 114 is positioned inside inner tube 112, as described above. A first end 122 abuts against cap 116, and is effectively sealed by the cap from diffusing drug therethrough. On the end of reservoir 114 opposite cap 116, the reservoir is preferably in direct contact with outer layer 110. As will be readily appreciated by one of ordinary skill in the art, as drug is released from reservoir 114, the reservoir may shrink or otherwise change shape, and therefore may not fully or directly contact outer layer 110 at the end of the reservoir opposite cap 116. As outer layer 110 is permeable to the drug in reservoir 114, the drug is free to diffuse out of the reservoir along a first flow path 124 into portions of outer layer 110 immediately adjacent to the open end of the reservoir. From outer layer 110, the drug is free to diffuse along flow paths 126 out of the outer layer and into the tissue or other anatomical structure in which device 100 is inserted or implanted. Optionally, holes can be formed through inner layer 112 to add additional flow paths 126 between reservoir 114 and permeable outer layer 110.

Figure 5:
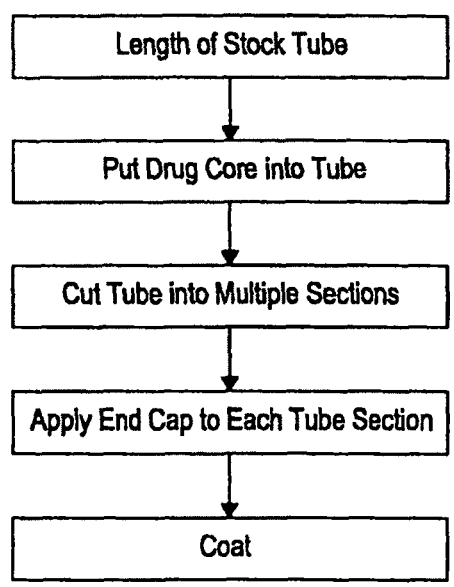
FIG. 5 schematically illustrates an embodiment of a method in accordance with the present invention of fabricating a drug delivery device.)

As discussed above, by providing inner tube 112 of a relatively rigid material, it is possible to more easily manufacture device 100. By way of example only and not of limitation, referring to FIG. 5, according to a first embodiment of a process of forming device 100, a length of tube stock material is taken as the starting material. Into the open end of tube 112, opposite cap 116, a drug reservoir 114 is inserted, injected, or otherwise positioned, depending on how viscous the drug reservoir material is when positioned in the tube. If reservoir 114 is relatively stiff, i.e., is very viscous or solid, the reservoir can be inserted into tube 112, as with a plunger, pushrod, or the like. If reservoir 114 is relatively flaccid or fluid, i.e., is not very viscous, the reservoir can be poured, injected, or drawn into the tube (e.g., by vacuum). The length of tube, including the drug core, is then cut into multiple sections, each of which form a tube 112. Cap 116 is joined to one end of tube 112, thus forming a closed, cup- or vessel-like structure. Thereafter, owing to the relative rigidity of inner tube 112, the inner tube and cap 116 can be handled with relative ease, because the inner tube is sized and formed of a material so that it is capable of supporting its own weight, the weight of tap 116, and the weight of reservoir 114, without collapsing. Thereafter, the tube can be coated.

According to yet another embodiment of a process for manufacturing in accordance with the present invention, reservoir 114 can be inserted into a mold, along with cap 116, and inner tube 112 can be molded around the reservoir and cap. Further alternatively, cap 116 can be formed integrally with inner tube 112.

By way of contrast, prior devices, including those which include merely a coating around a drug-containing reservoir, at this stage in the manufacturing process must be specially handled by, for example, forming and placing the reservoir in a carrier which supports the coating and reservoir during handling. As will be readily appreciated by one of ordinary skill in the art, elimination by the present invention of such additional manufacturing steps and components simplifies the manufacturing process, which in turn can lead to improvements in rejection rates and reductions in costs.

FIG. 1 illustrates only the positions of the several components of device 100 relative to one another, and for ease of illustration shows outer layer 110 and inner tube 112 as having approximately the same wall thickness. While the walls of outer layer 110 and inner tube 112 may be of approximately the same thickness, the inner tube's wall thickness can be significantly thinner or thicker than that of the outer layer within the spirit and scope of the present invention. Additionally, device 100 is preferably cylindrical in shape, for which a transverse cross-section (not illustrated) will show circular cross-sections of the device. While it is preferred to manufacture device 100 as a cylinder with circular cross-sections, it is also within the scope of the present invention to provide cap 116, reservoir 114, inner tube 112, and/or outer layer 110 with other cross-sections, such as ovals, ellipses, rectangles, including squares, triangles, as well as any other regular polygon or irregular shapes. Furthermore, device 100 can optionally further include a second cap (not illustrated) on the end opposite cap 116; such a second cap could be used to facilitate handling of the device during fabrication, and would include at least one through hole for allowing drug from reservoir 114 to flow from the device.

Figure 2:
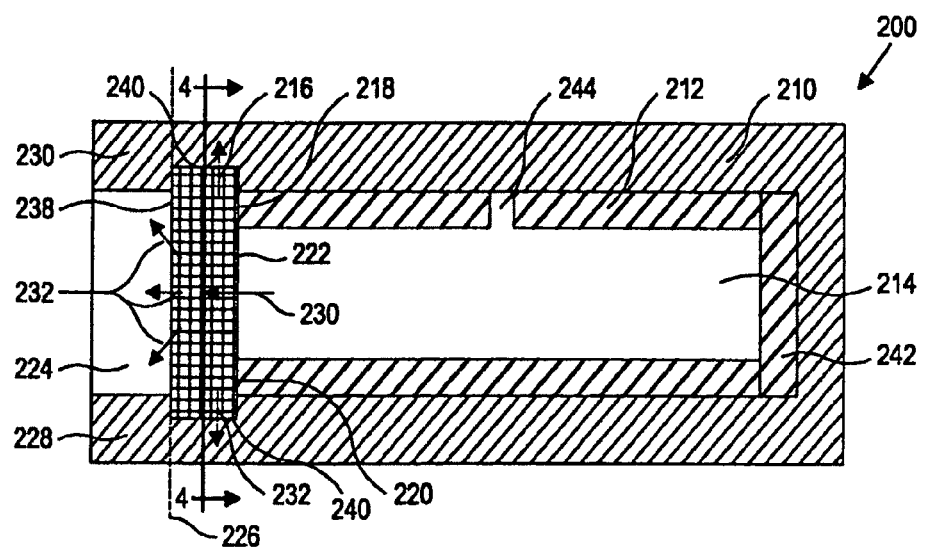
FIG. 2 is an enlarged cross-sectional illustration of a second embodiment of a sustained release drug delivery device in accordance with the present invention.

FIG. 2 illustrates a device 200 in accordance with a second exemplary embodiment of the present invention. Device 200 includes an impermeable inner tube 212, a reservoir 214, and a permeable plug 216. Device 200 optionally and preferably includes an impermeable outer layer 210, which adds mechanical integrity and dimensional stability to the device, and aids in manufacturing and handling the device. As illustrated in FIG. 2, reservoir 214 is positioned in the interior of inner tube 212, in a fashion similar to reservoir 114 and inner tube 112, described above. Plug 216 is positioned at one end of inner tube 212, and is joined to the inner tube at end 218, 220 of the inner tube. While plug 216 may extend radially beyond inner tube 212, as illustrated in FIG. 2, the plug may alternatively have substantially the same radial extent as, or a slightly smaller radial extent than, the inner tube, within the spirit and scope of the present invention. As plug 216 is permeable to the agent contained in reservoir 214, the agent is free to diffuse through the plug from the reservoir. Plug 216 therefore must have a radial extent which is at least as large as the radial extent of reservoir 214, so that the only diffusion pathway 230 out of the reservoir is through the plug. On the end of inner tube 212 opposite plug 216, the inner tube is closed off or sealed only by outer layer 210, as described below. Optionally, an impermeable cap 242, which can take the form of a disc, is positioned at the end of reservoir opposite plug 216. When provided, cap 242 and inner tube 212 can be formed separately and assembled together, or the inner tube and the cap can be formed as a single, integral, monolithic element.

Outer tube or layer 210, when provided, at least partially, and preferably completely surrounds or envelopes inner tube 212, reservoir 214, plug 216, and optional cap 242, except for an area immediately adjacent to the plug which defines a port 224. Port 224 is, in preferred embodiments, a hole or blind bore which leads to plug 216 from the exterior of the device. As outer layer 210 is formed of a material which is impermeable to the agent in reservoir 214, the ends of inner tube 212 and reservoir 214 opposite plug 216 are effectively sealed off, and do not include a diffusion pathway for the agent to flow from the reservoir. According to a preferred embodiment, port 224 is formed immediately adjacent to plug 216, on an end 238 of the plug opposite end 222 of reservoir 214. Plug 216 and port 224 therefore include diffusion pathways 230, 232, through the plug and out of device 200, respectively.

While port 224 in the embodiment illustrated in FIG. 2 has a radial extent which is approximately the same as inner tube 212, the port can be sized to be larger or smaller, as will be readily apparent to one of ordinary skill in the art. For example, instead of forming port 224 radially between portions 228, 230 of outer layer 210, these portions 228, 230 can be removed up to line 226, to increase the area of port 224. Port 224 can be further enlarged, as by forming outer layer 210 to extend to cover, and therefore seal, only a portion or none of the radial exterior surface 240 of plug 216, thereby increasing the total surface area of port 224 to include a portion or all of the outer surface area of the plug.

Figure 4:
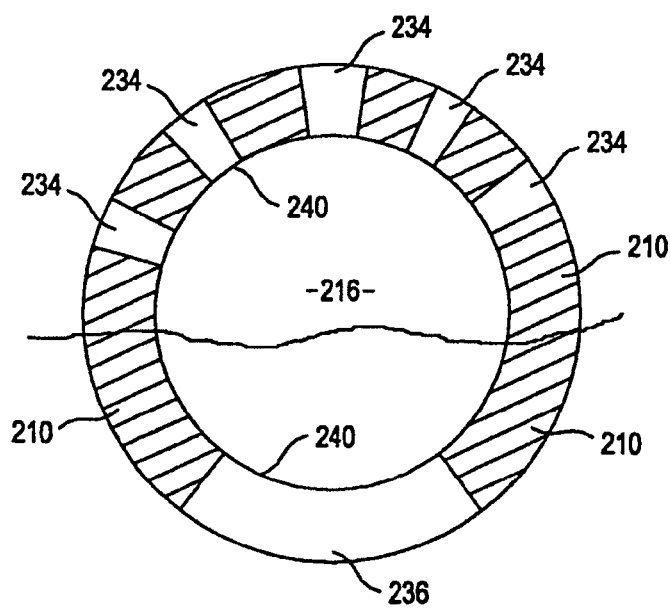
FIG. 4 is a cross-sectional illustration of the embodiment illustrated in FIG. 2, taken at line 4-4.

In accordance with yet another embodiment of the present invention, port 224 of device 200 can be formed immediately adjacent to radial external surface 240 of plug 216, in addition to or instead of being formed immediately adjacent to end 238 of the plug. As illustrated in FIG. 4, port 224 can include portions 234, 236, which extend radially away from plug 216. These portions can include large, continuous, circumferential and/or longitudinal portions 236 of plug 216 which are not enveloped by outer layer 210, illustrated in the bottom half of FIG. 4, and/or can include numerous smaller, circumferentially spaced apart portions 234, which are illustrated in the top half of FIG. 4. Advantageously, providing port 224 immediately adjacent to radial external surface 240 of plug 216, as numerous, smaller openings 234 to the plug, allows numerous alternative pathways for the agent to diffuse out of device 200 in the event of a blockage of portions of the port. Larger openings 236, however, benefit from a relative ease in manufacturing, because only a single area of plug 216 need be exposed to form port 224.

According to yet another embodiment of the present invention, plug 216 is formed of an impermeable material and outer layer 210 is formed of a permeable material. A hole or holes are formed, e.g., by drilling, through one or more of inner layer 212, cap 242, and plug 216, which permit drug to be released from reservoir 214 through outer layer 210. According to another embodiment, plug 216 is eliminated as a separate member, and permeable outer layer 210 completely envelopes inner tube 212 and cap 242 (if provided). Thus, the diffusion pathways 230, 232 are through outer layer 210, and no separate port, such as port 224, is necessary. By completely enveloping the other structures with outer layer or tube 210, the system 200 is provided with further dimensional stability. Further optionally, plug 216 can be retained, and outer layer 210 can envelop the plug as well.

According to yet another embodiment of the present invention, inner tube 212 is formed of a permeable material, outer layer 210 is formed of an impermeable material, and cap 242 is formed of either a permeable or an impermeable material. Optionally, cap 242 can be eliminated. As described above, as outer layer 210 is impermeable to the agent in reservoir 214, plug 216, port 224, and optional ports 234, 236, are the only pathways for passage of the agent out of device 200.

In a manner similar to that described above with reference to FIG. 1, the use of a relatively rigid inner tube 212 allows device 200 to be more easily manufactured. According to one embodiment of a process for forming device 200, the combination of plug 216 and inner tube 212 is loaded with reservoir 214, similar to how reservoir 114 is loaded into inner tube 112 and cap 116, described above. Thereafter, if provided, outer layer 210 is formed around plug 216, inner tube 212, reservoir 214, and cap 242 when provided, to form an impermeable outer layer, for reasons discussed above. To form port 224, material is then removed from outer layer 210 to expose a portion of or all of the outer surface of plug 216, as described above. Alternatively, port 224 can be formed simultaneously with the formation of outer layer 210, as by masking the desired area of plug 216.

According to yet another embodiment of a process for manufacturing in accordance with the present invention, reservoir 214 can be inserted into a mold, along with plug 216 and cap 242, and inner tube 112 can be molded around the reservoir, plug, and cap.

The shape of device 200 can be, in a manner similar to that described above with respect to device 100, any of a large number of shapes and geometries. Furthermore, both device 100 and device 200 can include more than one reservoir 114, 214, included in more than one inner tube 112, 212, respectively, which multiple reservoirs can include diverse or the same agent or drug for diffusion out of the device. In device 200, multiple reservoirs 214 can be positioned to abut against only a single plug 216, or each reservoir 214 can have a dedicated plug for that reservoir. Such multiple reservoirs can be enveloped in a single outer layer 110, 210, as will be ready appreciated by one of ordinary skill in the art.

Figure 3:
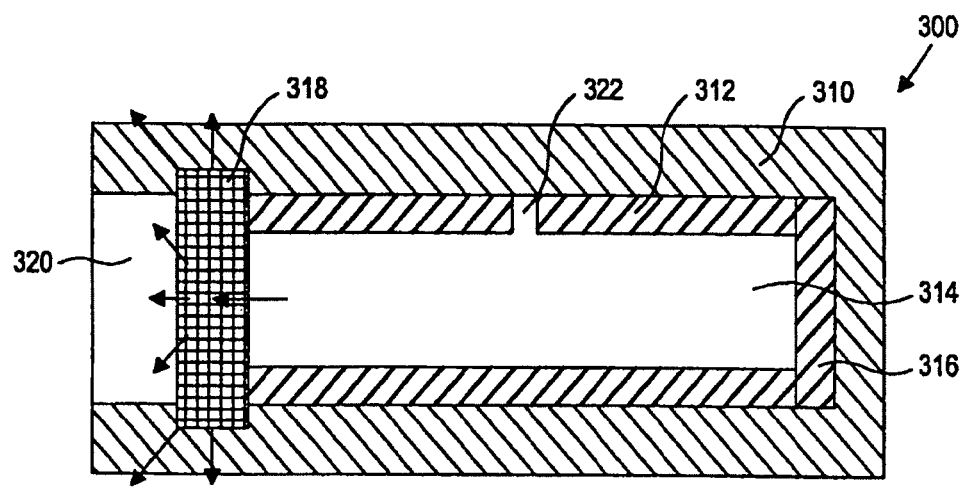
FIG. 3 is an enlarged cross-sectional illustration of a third embodiment of a sustained release drug delivery device in accordance with the present invention.

Turning now to FIG. 3, FIG. 3 illustrates a device 300 in accordance with a third exemplary embodiment of the present invention. Device 300 includes a permeable outer layer 310, an impermeable inner tube 312, a reservoir 314, an impermeable cap 316, and a permeable plug 318. A port 320 communicates plug 318 with the exterior of the device, as described above with respect to port 224 and plug 216. Inner tube 312 and cap 316 can be formed separately and assembled together, or the inner tube and the cap can be formed as a single, integral, monolithic element. The provision of permeable outer layer 310 allows the therapeutical agent in reservoir or drug core 314 to flow through the outer layer in addition to port 320, and thus assists in raising the overall delivery rate. Of course, as will be readily appreciated by one of ordinary skill in the art, the permeability of plug 318 is the primary regulator of the drug delivery rate, and is accordingly selected. Additionally, the material out of which outer layer 310 is formed can be specifically chosen for its ability to adhere to the underlying structures, cap 316, tube 312, and plug 318, and to hold the entire structure together. Optionally, a hole or holes 322 can be provided through inner tube 312 to increase the flow rate of drug from reservoir 314.

The invention further relates to a method for treating a mammalian organism to obtain a desired local or systemic physiological or pharmacological effect. The method includes administering the sustained release drug delivery system to the mammalian organism and allowing the agent effective in obtaining the desired local or systemic effect to pass through outer layer 110 of device 100, plug 216 of device 200, or plug 318 and outer layer 310 of device 300 to contact the mammalian organism. The term administering, as used herein, means positioning, inserting, injecting, implanting, or any other means for exposing the device to a mammalian organism. The route of administration depends on a variety of factors including type of response or treatment, type of agent, and preferred site of administration.

The devices in certain embodiments have applicability in providing a controlled and sustained release of agents effective in obtaining a desired local or systemic physiological or pharmacological effect relating at least to the following areas: treatment of cancerous primary tumors, (e.g., glioblastoma); inhibition of neovascularization, including ocular neovascularization; edema, including ocular edema; inflammation, including ocular inflamation; chronic pain; arthritis; rheumatic conditions; hormonal deficiencies such as diabetes and dwarfism; and modification of the immune response such as in the prevention of transplant rejection and in cancer therapy. A wide variety of other disease states may also be prevented or treated using the drug delivery device of the present invention. Such disease states are known by those of ordinary skill in the art. For those not skilled in the art, reference may be made to Goodman and Gilman, *The Pharmacological Basis of Therapeutics,* 8th Ed., Pergamon Press, NY, 1990; and *Remington's Pharmaceutical Sciences,* 18th Ed., Mack Publishing Co., Easton, Pa., 1990; both of which are incorporated by reference herein.

In addition, the devices are suitable for use in treating mammalian organisms infected with HIV and AIDS-related opportunistic infections such as cytomegalovirus infections, toxoplasmosis, pneumocystis carinii, and mycobacterium avium intercellular.

The devices are particularly suitable for treating ocular conditions such as glaucoma, proliferative vitreoretinopathy, macular edema, including diabetic macular edema, age-related macular degeneration, diabetic retinopathy, uveitis, ocular neovascularization, and ocular infection. The devices are also particularly suitable for use as an ocular device in treating mammalian organisms, both human and for veterinarian use, suffering from ocular histoplasmosis, wherein the device is surgically implanted within the vitreous of the eye.

As described above, the inner core or reservoir contains an agent effective in obtaining a desired local or systemic physiological or pharmacological effect. The following classes of agents could be incorporated into the devices of the present invention: anesthetics and pain killing agents such as lidocaine and related compounds and benzodiazepam and related compounds; anti-cancer agents such as 5-fluorouracil, adriamycin and related compounds; anti-inflammatory agents such as 6-mannose phosphate; anti-fungal agents such as fluconazole and related compounds; anti-viral agents such as trisodium phosphomonoformate, trifluorothymidine, acyclovir, ganciclovir, DDI, DDC, and AZT; cell transport/mobility impending agents such as colchicine, vincristine, cytochalasin B, and related compounds; antiglaucoma drugs such as beta-blockers: timolol, betaxol, atenalol, etc; immunological response modifiers such as muramyl dipeptide and related compounds; peptides and proteins such as cyclosporin, insulin, growth hormones, insulin related growth factor, heat shock proteins and related compounds; steroidal compounds such as dexamethasone, prednisolone and related compounds; corticosteroids such as fluocinolone acetonide and related compounds; and carbonic anhydaze inhibitors.

In addition to the above agents, other agents are suitable for administration to the eye and its surrounding tissues to produce a local or a systemic physiologic or pharmacologic beneficial effect. Examples of such agents include neuroprotectants such as nimodipine and related compounds; antibiotics such as tetracycline, chlortetracycline, bacitracin, neomycin, polymyxin, gramicidin, oxytetracycline, chloramphenicol, gentamycin, and erythromycin; antibacterials such as sulfonamides, sulfacetamide, sulfamethizole and, sulfisoxazole; antivirals, including idoxuridine; and other antibacterial agents-such as nitrofurazone and sodium propionate; antiallergenics such as antazoline, methapyriline, chlorpheniramine, pyrilamine, and prophenpyridamine; anti-inflammatories such as hydrocortisone, hydrocortisone acetate, dexamethasone 21-phosphate, fluocinolone, medrysone, methylprednisolone, prednisolone 21-phosphate, prednisolone acetate, fluorometalone, betamethasone, and triminolone; decongestants such as phenylephrine, naphazoline, and tetrahydrazoline; miotics and anti-cholinesterase such as pilocarpine, eserine salicylate, carbachol, di-isopropyl fluorophosphate, phospholine iodine, and demecarium bromide; mydriatics such as atropine sulfate, cyclopentolate, homatropine, scopolamine, tropicamide, eucatropine, and hydroxyamphetamine; sympathomimetics such as epinephrine; and prodrugs such as those described in *Design of Prodrugs,* edited by Hans Bundgaard, Elsevier Scientific Publishing Co., Amsterdam, 1985. Once again, reference may be made to any standard pharmaceutical textbook such as *Remington's Pharmaceutical Sciences* for the identify of other agents.

Any pharmaceutically acceptable form of such a compound may be employed in the practice of the present invention, i.e., the free base or a pharmaceutically acceptable salt or ester thereof. Pharmaceutically acceptable salts, for instance, include sulfate, lactate, acetate, stearate, hydrochloride, tartrate, maleate, and the like.

A large number of materials can be used to construct the devices of the present invention. The only requirements are that they are inert, non-immunogenic, and of the desired permeability, as described above.

Materials that may be suitable for fabricating devices 100, 200, and 300 include naturally occurring or synthetic materials that are biologically compatible with body fluids and/or eye tissues, and essentially insoluble in body fluids with which the material will come in contact. The use of rapidly dissolving materials or materials highly soluble in eye fluids are to be avoided since dissolution of the outer layers 110, 210, 310 would affect the constancy of the drug release, as well as the capability of the system to remain in place for a prolonged period of time.

Naturally occurring or synthetic materials that are biologically compatible with body fluids and eye tissues and essentially insoluble in body fluids which the material will come in contact include, but are not limited to: ethyl vinyl acetate, polyvinyl acetate, cross-linked polyvinyl alcohol, cross-linked polyvinyl butyrate, ethylene ethylacrylate copolymer, polyethyl hexylacrylate, polyvinyl chloride, polyvinyl acetals, plasiticized ethylene vinylacetate copolymer, polyvinyl alcohol, polyvinyl acetate, ethylene vinylchloride copolymer, polyvinyl esters, polyvinylbutyrate, polyvinylformal, polyamides, polymethylmethacrylate, polybutylmethacrylate, plasticized polyvinyl chloride, plasticized nylon, plasticized soft nylon, plasticized polyethylene terephthalate, natural rubber, polyisoprene, polyisobutylene, polybutadiene, polyethylene, polytetrafluoroethylene, polyvinylidene chloride, polyacrylonitrile, cross-linked polyvinylpyrrolidone, polytrifluorochloroethylene, chlorinated polyethylene, poly (1,4'-isopropylidene diphenylene carbonate), vinylidene chloride, acrylonitrile copolymer, vinyl chloride-diethyl fumerale copolymer, silicone rubbers, especially the medical grade polydimethylsiloxanes, ethylene-propylene rubber, silicone-carbonate copolymers, vinylidene chloride-vinyl chloride copolymer, vinyl chloride-acrylonitrile copolymer, vinylidene chloride-acrylonitride copolymer, gold, platinum, and (surgical) stainless steel.

Specifically, outer layer 210 of device 200 may be made of any of the above-listed polymers or any other polymer which is biologically compatible with body fluids and eye tissues, essentially insoluble in body fluids which the material will come in contact, and essentially impermeable to the passage of the effective agent. The term impermeable, as used herein, means that the layer will not allow passage of the effective agent at a rate required to obtain the desired local or systemic physiological or pharmacological effect.

When inner tube 112, 212, 312 is be selected to be impermeable, as described above, to the passage of the agent from the inner core or reservoir out to adjacent portions of the device, the purpose is to block the passage of the agent to those portions of the device, and thus control the release of the agent out of the drug delivery device through outer layer 110, plug 216, and plug 318.

The composition of outer layer 110, e.g., the polymer, must be selected so as to allow the above-described controlled release. The preferred composition of outer layer 110 and plug 216 will vary depending on such factors as the active agent, the desired rate of control, and the mode of administration. The identity of the active agent is important since the size of the molecule, for instance, is critical in determining the rate of release of the agent into the outer layer 110 and plug 216.

Caps 116, 242, 316 are essentially impermeable to the passage of the effective agent and may cover a portion of the inner tube not covered by the outer layer. The physical properties of the material, preferably a polymer, used for the caps can be selected based on their ability to withstand subsequent processing steps (such as heat curing) without suffering deformation of the device. The material, e.g., polymer, for impermeable outer layer 210 can be selected based on the ease of coating inner tube 212. Cap 116 can be formed of one of a number of materials, including PTFE, polycarbonate, polymethyl methacrylate, polyethylene alcohol, high grades of ethylene vinyl acetate (9% vinyl, content), and polyvinyl alcohol (PVA). Inner tubes 112, 212, 312 can be formed of one of a number of materials, including PTFE, polycarbonate, polymethyl methacrylate, polyethylene alcohol, high grades of ethylene vinyl acetate (9% vinyl, content), and polyvinyl alcohol. Plugs 216, 318 can be formed of one of a number of materials, including cross-linked PVA, as described below.

Outer layers 110, 210, 310, and plugs 216, 318 of the device of the present invention must be biologically compatible with body fluids and tissues, essentially insoluble in body fluids which the material will come in contact, and outer layer 110 and plugs 216, 318 must be permeable to the passage of the agent or composition effective in obtaining the desired effect.

The effective agent diffuses in the direction of lower chemical potential, i.e., toward the exterior surface of the device. At the exterior surface of the device, equilibrium is again established. When the conditions on both sides of outer layer 110 or plugs 216, 318 are maintained constant, a steady state flux of the effective agent will be established in accordance with Fick's Law of Diffusion. The rate of passage of the drug through the material by diffusion is generally dependent on the solubility of the drug therein, as well as on the thickness of the wall. This means that selection of appropriate materials for fabricating outer layer 110 and plug 216 will be dependent on the particular drug to be used.

The rate of diffusion of the effective agent through a polymeric layer of the present invention may be determined via diffusion cell studies carried out under sink conditions. In diffusion cell studies carried out under sink conditions, the concentration of drug in the receptor compartment is essentially zero when compared to the high concentration in the donor compartment. Under these conditions, the rate of drug release is given by:

$$Q/t = (D \cdot K \cdot A \cdot DC)/h$$

where Q is the amount of drug released, t is time, D is the diffusion coefficient, K is the partition coefficient, A is the surface area, DC is the difference in concentration of the drug across the membrane, and h is the thickness of the membrane.

In the case where the agent diffuses through the layer via water filled pores, there is no partitioning phenomena. Thus, K can be eliminated from the equation. Under sink conditions, if release from the donor side is very slow, the value DC is essentially constant and equal to the concentration of the donor compartment. Release rate therefore becomes dependent on the surface area (A), thickness (h), and diffusivity (D) of the membrane. In the construction of the devices of the present invention, the size (and therefore, surface area) is mainly dependent on the size of the effective agent.

Thus, permeability values may be obtained from the slopes of a Q versus time plot. The permeability P, can be related to the diffusion coefficient D, by:

$$P = (K \cdot D)/h$$

Once the permeability is established for the material permeable to the passage of the agent, the surface area of the agent that must be coated with the material impermeable to the passage of the agent may be determined. This is done by progressively reducing the available surface area until the desired release rate is obtained.

Exemplary microporous materials suitable for use as outer layer 110 and plugs 216, 318, for instance, are described in U.S. Pat. No. 4,014,335, which is incorporated herein by reference in its entirety. These materials include cross-linked polyvinyl alcohol, polyolefins or polyvinyl chmorides or cross-linked gelatins; regenerated, insoluble, non-erodible cellulose, acylated cellulose, esterified celluloses, cellulose acetate propionate, cellulose acetate butyrate, cellulose acetate phthalate, cellulose acetate diethyl-aminoacetate; polyurethanes, polycarbonates, and microporous polymers formed by co-precipitation of a polycation and a polyanion modified insoluble collagen. Cross-linked polyvinyl alcohol is preferred for both outer layer 110 and plugs 216, 318.

The devices of the present invention may be made in a wide variety of ways, portions of which are described in greater detail above. Once the reservoir and inner tube have been assembled along with caps 116, 242 or plugs 216, 318, the outer layer may be applied. The outer layer may be applied by dipping the device one or more times in a solution containing the desired polymer. Optionally, the outer layer may be applied by dropping, spraying, brushing or other means of coating the outer surface of the device with the polymer solution. When using a polyvinyl alcohol solution to obtain the outer layer, the desired thickness may be obtained by applying several coats. Each coat may be dried prior to applying the next coat. Finally, the device may be heated to adjust the permeability of outer layer 110 or plugs 216, 318.

Impermeable polymer layers in devices in accordance with the present invention should be thick enough to prevent release of drug across them except for the area not covered, e.g., port 224. Due to the desirability of minimizing the size of the implantable devices, the thickness of an impermeable layer therefore can be between about 0.01 and about 2 millimeters, preferably between about 0.01 and about 0.5 millimeters, most preferably between about 0.01 and about 0.2 millimeters.

Caps 116, 242 should also be thick enough to prevent drug release across it. Due to the desirability of minimizing the size of the implants, the thickness of the impermeable cap 116 can be between about 0.01 and about 2 millimeters, preferably between about 0.01 and about 0.5 millimeter, most preferably between about 0.01 and about 0.2 millimeter.

The above description of how to make the devices of the present invention is merely illustrative and should not be considered as limiting the scope of the invention in any way, as various compositions are well known by those skilled in the art. In particular, the methods of making the device depends on the identity of the active agent and polymers selected. Given the active agent, the composition, of the outer layers, the inner tube, the plug, and the cap, one skilled in the art could easily make the devices of the present invention using conventional coating techniques.

The method for treating a mammalian organism to obtain a desired local or systemic physiological or pharmacological effect includes administering the sustained release drug delivery device of the present invention to the mammalian organism and allowing the agent to pass through the device to come in direct contact with the mammalian organism.

The drug delivery system of the present invention may be administered to a mammalian organism via any route of administration known in the art. Such routes of administration include intraocular, oral, subcutaneous, intramuscular, intraperitoneal, intranasal, dermal, into the brain, including intracranial and intradural, into the joints, including ankles, knees, hips, shoulders, elbows, wrists, directly into tumors, and the like. In addition, one or more of the devices may be administered at one time, or more than one agent may be included in the inner core or reservoir, or more than one reservoir may be provided in a single device.

The drug delivery system of the present invention is particularly suitable for direct implantation into the vitreous of the eye and for application to an intraocular lens.

These methods of administration and technique for their preparation are well known by those of ordinary skill in the art. Techniques for their preparation are set forth in *Remington's Pharmaceutical Sciences.*

The drug delivery system may be administered for a sufficient period of time and under conditions to allow treatment of the disease state of concern.

For localized drug delivery, the devices may be surgically implanted at or near the site of action. This is the case for devices of the present invention used in treating ocular conditions, primary tumors, rheumatic and arthritic conditions, and chronic pain.

For systemic relief, the devices may be implanted subcutaneously, intramuscularly, intraarterially, intrathecally, or intraperitoneally. This is the case when devices are to give sustained systemic levels and avoid premature metabolism. In addition, such devices may be administered orally.

In one embodiment of the invention, an ocular device containing fluocinolone acetonide as the effective agent in a therapeutically effective amount to reduce or prevent ocular neovascularization may be prepared. Such devices may be used to effectively combat and inhibit undesirable ocular neovascularization, edema, or inflamation when surgically implanted into the vitreous of the eye. Such devices may remain in the vitreous permanently after treatment is complete. The preferred amount of fluocinolone acetonide used in these devices ranges from about 0.01 mg to about 40 mg. More preferably, such devices contain from about 0.1 mg to about 6 mg of fluocinolone acetonide. These preferred ranges may provide sustained release of the fluocinolone acetonide for a period of from several hours to over five years. Preferred permeable layers in accordance with the present invention are formed of polyvinyl alcohol, which is preferably crosslinked. Preferred impermeable portions of devices 100, 200, e.g., cap 116 and inner tubes 112, 212, are formed of PTFE or ethyl vinyl alcohol.

When such devices are prepared for implantation within the vitreous of the eye, it is preferred that the device does not exceed about 7 millimeters in any direction, so that the device can be inserted through a less than 7 millimeter incision. Thus, the cylindrical devices illustrated in FIGS. 1 and 2 would preferably not exceed 7 millimeters in height or 3 millimeters in diameter. The preferred thickness of the walls of inner tubes 112, 212 ranges between about 0.01 mm and about 1.0 mm. The preferred thickness of the wall of outer layer 110 ranges between about 0.01 mm and about 1.0 mm. The preferred thickness of the wall of outer layer 210 ranges between about 0.01 mm and 1.0 mm.

While the above described embodiments of the invention are described in terms of preferred ranges of the amount of effective agent, and preferred thicknesses of the preferred layers, these preferences are by no means meant to limit the invention. As would be readily understood by one skilled in the art, the preferred amounts, materials and dimensions depend on the method of administration, the effective agent used, the polymers used, the desired release rate and the like. Likewise, actual release rates and release duration depend on a variety of factors in addition to the above, such as the disease state being treated, the age and condition of the patient, the route of administration, as well as other factors which would be readily apparent to those skilled in the art. All of the foregoing U.S. Patents and other publications are expressly incorporated by reference herein in each of their entireties.

From the foregoing description, one of ordinary skill in the art can easily ascertain the essential characteristics of the instant invention, and without departing from the spirit and scope thereof, can make various changes and/or modifications of the invention to adapt it to various usages and conditions. As such, these changes and/or modifications are properly, equitably and intended to be, within the full range of equivalence of the following claims.

What is claimed is:

1. A method of manufacturing a sustained drug delivery system, comprising
    positioning a drug core in an impermeable tube, said drug core containing a therapeutically effective amount of an active agent, wherein said impermeable tube is dimensionally stable and capable of supporting its own weight;
    cross-sectionally cutting the tube into sections; and
    forming a permeable outer layer around at least a portion of a section.

2. The method according to claim 1, wherein the outer layer is formed by dipping, dropping, spraying, or brushing the section with a solution of polymer.

3. The method according to claim 1, further comprising positioning an end member to said tube to form a closed-end tube, said end member selected from an impermeable cap and a permeable plug.

4. A method in accordance with claim 3, wherein positioning an end member comprises joining said end member to a length of said tube to form a vessel-shaped member.

5. A method in accordance with claim 4, wherein said joining comprises coupling an impermeable cap to said length of tube.

6. The method of claim 1, wherein the active agent is fluocinolone acetonide.

* * * * *